United States Patent [19]

Olerud

[11] Patent Number: 5,057,109
[45] Date of Patent: Oct. 15, 1991

[54] FIXING INSTRUMENTS FOR SPINAL SURGERY

[76] Inventor: Sven Olerud, 710 11 Lännaholm, Malmen, Sweden

[21] Appl. No.: 489,703

[22] Filed: Mar. 7, 1990

[30] Foreign Application Priority Data

Oct. 16, 1989 [SE] Sweden .................... 8903403

[51] Int. Cl.$^5$ .................. A61F 5/04; A61F 5/00
[52] U.S. Cl. ........................ 606/61; 606/72; 128/69
[58] Field of Search ............ 606/57, 59, 60, 61, 606/67, 69, 70, 64, 65, 104, 72, 73; 128/69

[56] References Cited

U.S. PATENT DOCUMENTS

| | | | |
|---|---|---|---|
| 2,393,831 | 1/1946 | Stader | 606/59 |
| 2,631,574 | 3/1953 | Purificato | 606/23 |
| 3,693,616 | 9/1972 | Roaf | 606/61 |
| 3,741,205 | 6/1973 | Markolf | 606/73 |
| 4,175,555 | 11/1979 | Herbert | 606/73 |
| 4,493,317 | 1/1985 | Klaue | 606/73 |
| 4,548,199 | 10/1985 | Agee | 606/57 |
| 4,628,919 | 12/1986 | Clyburn | 606/57 |
| 4,757,809 | 7/1988 | Koeneman | 606/59 |
| 4,771,767 | 9/1988 | Steffe | 128/69 |

FOREIGN PATENT DOCUMENTS

WO87/01026 1/1987 European Pat. Off. .

*Primary Examiner*—Robert A. Hafer
*Assistant Examiner*—Michael Brown
*Attorney, Agent, or Firm*—Finnegan, Henderson, Farabow, Garrett & Dunner

[57] ABSTRACT

A fixing instrument for spinal surgery comprises two units (1,36) which by means of bone screws (6,7) each may be secured to a vertebra. One of these units (1) includes a block (2) having two rotatably mounted bone screws (6,7) which by means of special locking means (16) are secured against turning after the bone screws have been screwed in.

17 Claims, 2 Drawing Sheets

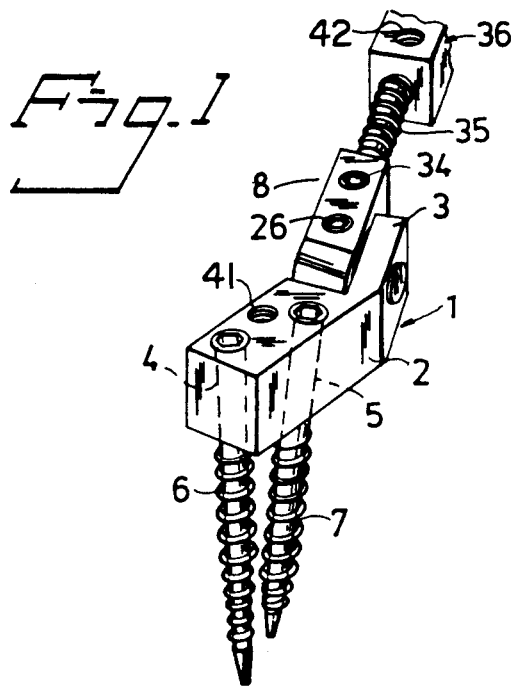
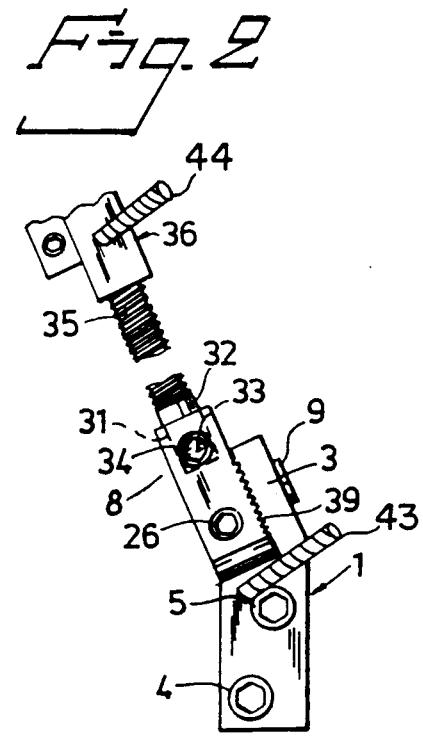
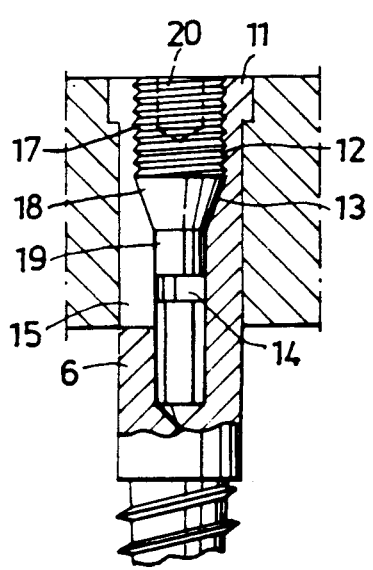
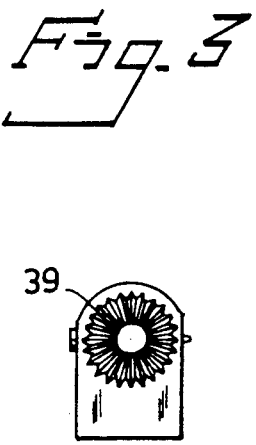

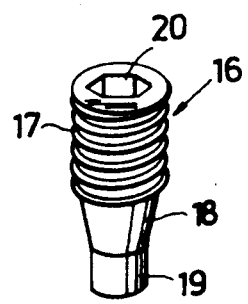
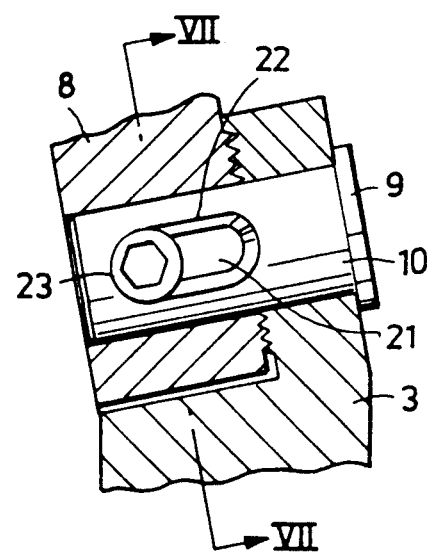
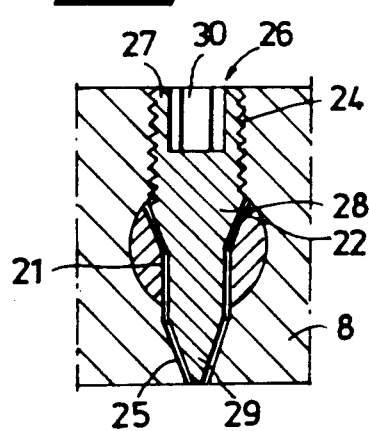
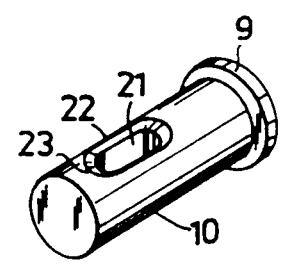
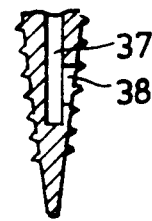

FIXING INSTRUMENTS FOR SPINAL SURGERY

BACKGROUND OF THE INVENTION

1. Field of the Invention

The present invention refers to an apparatus for fixation to human bone, and in particular to a human spine for use during spinal surgery.

More specifically it refers to such an instrument which includes at least two units which may be secured to spinal vertebrae by means of so called bone screws and which are connected to each other by connecting means, the connecting means being capable of varying their length such as screw spindles. One of said units is provided to be secured to the sacrum portion of the spine.

2. Description of the Related Art

A problem frequently encountered during surgery in the sacrum region involves the structure of the bone material to which the instrument is to be secured. The bone structure at the sacrum is spongy and often osteoporotic in nature. This is particularly true for elderly persons.

For this and other reasons, securing an instrument to the sacrum is effected by means of one and sometimes two bone screws. The type of bone screws which hitherto have been suggested have not resulted in the strong anchoring which is a necessity for the intended operation.

Thus the object of an invention is to overcome this disadvantage and to provide an instrument which rapidly and easily may be secured in the most reliable manner.

A further object is to accomplish a hinge connection between the unit secured to the sacrum and one or several vertebrae situated above the sacrum, without being hindered by the angular condition of this portion of the spine, thereby making it possible to lock a setting even after having screwed in the bone screws.

A third object is to provide an instrument which makes it possible for the surgeon to accomplish all the settings and lockings from one direction and preferably by means of one single tool.

Additional objects and advantages of the invention will be set forth in the description which follows, and in part will be obvious from the description, or may be learned by practice of the invention. The object and advantages may be realized by means of the instrumentaties and combinations particularly pointed out in the appended claims.

SUMMARY OF THE INVENTION

The invention refers to a fixing instrument for spinal surgery. Instruments of that kind generally comprise two or more units which by means of so called bone screws can be fixed to bone portions, such as vertebrae. Such units are mutually connected by rigid connection means of variable length, such as screw spindles. Two pairs of such units are used in the operation. It is thus possible to effect the desired displacement and lock the instrument in a position in which the vertebrae are fixed in the desired positions relative to each other.

The invention is primarily intended to be used for surgery in the small of the back but from the following description it will be apparent that certain parts of the concept may be used also for entirely different purposes.

BRIEF DESCRIPTION OF THE DRAWINGS

The accompanying drawings show an exemplary embodiment of the invention as well as some detail constructions, where FIG. 1 is a perspective view of the fixing instrument of the present invention;

FIG. 2 is a plan view of the fixing instrument of FIG. 1;

FIG. 3 is a side view of a portion of the fixing instrument of FIG. 1;

FIG. 4 is an enlarged view of a section through a part of a block depicting a bone screw and locking means shown in FIG. 1;

FIG. 5 is a perspective view of the locking means shown in FIG. 4;

FIG. 6 is an enlarged partial view of a hinge connection of the fixing instrument;

FIG. 7 is a cross sectional view along line VII—VII in FIG. 6;

FIG. 8 is a perspective view of a bolt, forming part of the hinge connection according to FIGS. 6 and 7; and FIG. 9 is a partial sectional view and on an enlarged scale of a modified bone screw for use in the invention.

DESCRIPTION OF THE PREFERRED EMBODIMENTS

The instrument illustrated in FIG. 1 comprises a unit, generally designated as 1, which is intended to be secured to the sacrum. Unit 1 broadly consists of a block 2 which has a leg 3 extending obliquely in relation to the lengthwise direction of the block. In the block 2 there are provided two through holes 4,5 which have a different inclination, preferably in two different planes such that the center lines of the holes will diverge. Holes 4,5 are penetrated by bone screws 6,7 and it is obvious that the fastening to the bone will be very effective by the oblique position of the screws. The positions and angles of the holes 4,5 are further chosen so that the bone screws may not hurt nerve fibers and other things. Pivotably connected to block 1 is a second block 8. A bolt 10 having a head 9 is used to provide the pivotal connection. This pivotal connection will be described more in detail hereinafter.

In order to provide a strong anchoring of the block 2 to the sacrum it is necessary not only that the mentioned oblique position of the bone screws be present but also that the bone screws be prevented from rotation as well as from displacement. It is further desired that the fixing operation may be accomplished from the same direction as other manipulations of the instrument.

To this end the bone screws are designed as broadly shown in FIG. 4. The bone screw 6 has a head 11 and extending therefrom in an axial direction is an axial hole, which in the upper part of its extension is threaded 12, then tapered 13 and finally has the shape of a key handle, for instance an internal hexagon 14. By means of a number of axial slots 15 extending from the upper end of the bone screw the upper part of the bone screw is divided into a number of resilient segments which together constitute a chuck.

Due to the above configuration it is possible to thread the respective bone screws into the sacrum by means of a hexagonal key and that the bone screws then are permanently received in the block 2. In order to lock them in their threaded-in position, a locking means 16 shown in FIG. 5 is used. Locking means 16 has an outwardly threaded portion 17, intended to cooperate with the inwardly threaded portion 12 of the bone screw, a tapered portion 18, intended to cooperate with the internal tapered portion 13 of the bone screw, and an end stud 19 which preferably is guided in the hole 14 or a plain hole portion located thereabove. The locking means 16 further has in the upper end thereof an internal key handle 20 which preferably has the same size as the key handle 14.

The tapered portion 18 is so sized to apply pressure to the inner tapered portions 13 of the bone screw thereby causing the resilient segments thereof to expand outwardly, thus locking the respective bone screw to the block 2 in a very effective manner.

The pivotal connection between the blocks 1 and 8 mentioned above should be so designed that after the desired angle has been set, the blocks rapidly and simply can be locked in the set position. To this end it is designed in the manner shown in FIGS. 6–8. The above-mentioned bolt 10 is then provided to allow one of the unit parts 2,3 to rotate thereabout at the same time as it can be operated to fulfill a restricted axial movement in order to press the parts 2,3 and 8 against each other. In the illustrated embodiment this is achieved by the fact that the bolt 10 has a transverse aperture 21 which preferably is somewhat elongated in the axial direction. As particularly appears in FIG. 7 the substantially axially extending edge portions 22 of the hole are strongly chamfered for a purpose to be described. The left edge portion 23 in FIG. 6 of the aperture 21 preferably is also tapered. Through the block 8 and perpendicular to the aperture 21 for the bolt 10 there is provided an aperture (FIG. 7) which communicates with the journal hole for the bolt and in the first part of its extension is threaded and after having passed the journal hole constitutes a substantially narrower tapered portion 25.

A locking element designated as 26 has an outwardly threaded portion 27 which continues in a tapered portion 28 which in turn continues in a preferably cylindrical portion which ends in a narrower, tapered portion 29. The locking element has in the upper end thereof a key handle 30, which preferably has the same shape and size as the key handles 20 and 14 described above. The hole 24,25 is so positioned in relation to the hole 21 for the bolt 10 that the tapered portion 28 of the locking element will come into contact with the tapered left edge portion 23 of the aperture 21 when the locking element 26 is screwed into the aperture said tapered portion preferably having the same taper as the tapered portion 28. Continued screwing will then cause the bolt 10 to be displaced to the left in FIG. 6 by interaction of the tapered surfaces 23 and 28. Since the bolt 10 has a head which is in contact with the outer side of the leg 3 said displacement movement will cause the leg 3 to be displaced towards the block 8. In the end position leg 3 and block 8 will be effectively locked to each other. In said fully screwed position of the locking element the tapered end portion 29 thereof is in engagement with the tapered hole 25 of the block 8. In order to prevent the bolt from being expanded radially when the locking element is screwed in the edge portions 22 of the aperture 21 according to FIG. 7 are so much chamfered such that there will always be a certain clearance between the tapered portion 28 and said edge portions.

In order to further secure the setting of the instrument, the surfaces of the block 8 and the leg 3 which are in contact with each other are preferably provided with radially extending ridges and/or grooves (see FIG. 3) which by engaging each other effectively prevent any turning out of the set and locked position.

From FIG. 1 it can be seen that this locking action also is effected from the same direction as the other lockings and settings.

The unit now described is intended to be secured to the sacrum but the instrument also includes a unit which is secured to a vertebra and which is connected to the first-mentioned unit by means of a screw spindle or the like in such a manner that the units may be displaced in relation to each other by rotating the screw spindle.

As broadly shown in FIG. 2, the block 8 of the illustrated embodiment is provided with an axial bore 31 extending from the upper end thereof and in this bore a cylindrical portion 32 of a screw spindle 35 is received. This cylindrical portion has a circumferential groove 33, which engages a preferably tapered end portion of a locking screw 34 threaded into the block 8. The components are so sized that said locking screws when partly threaded in will fix the screw spindle 35 against displacement in the axial direction, but allow the rotation while the screw spindle is locked also against rotation when the locking screw is fully tightened.

The screw spindle 35 passes through a thread in a second unit 36, which as mentioned is provided to be secured to a vertebra by means of a bone screw under circumstances via a further unit. Since the unit 36 may be of the kind known by European Patent 0233930 this one will not be described more in detail.

As previously mentioned the bone at the sacrum often is so porous that it can be difficult to obtain a sufficiently effective anchoring of the fixing instrument in spite of the anchoring method here described.

According to the invention it is however possible even in such cases to attain a satisfactory fixing by designing the bone screws in the manner shown in FIG. 9.

As broadly depicted in FIG. 9, the bone screw, which per se may be designed according to FIG. 4 is provided with an axial bore 37, which extends towards the lower free end of the screw and there communicates with one or several openings 38 passing through the screw wall. After having threaded the respective bone screw fully or partly it is possible according to this embodiment to inject some kind of resin or the like by means of an injection device whereby said resin after hardening or curing with the bone material forms a structure which is capable of effectively holding the bone screws in question. By the aid of bone screws designed in such a manner it will thus be possible to improve the fastening capability of the instrument to the actual bone material while the operation takes place, providing reliable fixings even under less favorable conditions.

It is self-evident that certain of the solutions, units and components now described also may be used within other regions than the ones here described. Within the scope of the invention also lies the possibility to furnish the blocks 2 and 36 with securing means such as threaded holes 41,42 at the upper surface thereof making it possible to attach reposition handles 43,44 to said block and said reposition handles 43,44 may in turn be mutually connected by means of for instance screw spindles.

Additional advantages and modifications will readily occur to those skilled in the art. The invention, in its broader aspects, is therefore not limited to the specific details described herein. Accordingly, departures may be made from such details without departing from the spirit or scope of applicant's general inventive concept.

I claim:

1. An apparatus for fixation to a human spine during spinal surgery, comprising:

a first block portion having opposite surfaces and opposite ends, one of said surfaces disposed to be fixed adjacent to a portion of the spine, a projecting portion extending from one said end, and at least two spaced apertures obliquely inclined relative to one another penetrating said first block portion between said opposite surfaces;

fixing means disposed in each of said apertures for fixing said first block portion to the spine;

locking means for rigidly locking said fixing means within said apertures of said first block portion;

a second block portion disposed to be fixed to another portion of the spine; and attachment means for attaching said second block portion to said projecting portion in spaced relation to said first block portion, said attachment means including means for adjusting the space between said first and second block portions.

2. An apparatus according to claim 1, wherein said fixing means includes bone screws disposed in said spaced apertures, said screws being inclined relative to one another corresponding to the inclination of said apertures.

3. An apparatus according to claim 2, wherein each said bone screw includes a coaxial threaded bore and a plurality of axial slots defining a plurality of axial resilient portions.

4. An apparatus according to claim 3, wherein said locking means includes a generally frustoconical locking element configured for threadable insertion into said coaxial bore of said bone screw, having a tapered portion for expanding said plurality of resilient portions of said bone screw to fixedly engage said corresponding aperture.

5. An apparatus according to claim 4, wherein said bone screw includes a depression having a selected radius for insertion of an external operating member, and said locking element includes a depression for insertion of an external operating member having a radius equal to the selected radius of said depression in said bone screw.

6. An apparatus according to claim 1, wherein said attachment means includes a third block portion and pivotal attachment means for pivotably attaching said third block portion to said projecting portion, said second and third block portions being disposed to pivot in an arc relative to said first block portion.

7. An apparatus according to claim 6, wherein said adjusting means includes a spindle threadably attached at each end to said second block portion and said third block portion.

8. An apparatus according to claim 6, wherein said pivotal attachment means includes means for securing said second and third block portions in a plurality of selected positions in the arc angled relative to said first block portion.

9. An apparatus according to claim 6, further including means for preventing rotation of said spindle, whereby further operation of said adjusting means is prevented.

10. An apparatus according to claim 1, wherein said fixing means includes an externally threaded bone screw, said bone screw including an axial bore and a radial aperture connecting said bore to said external threads, for insertion of reinforcement means for reinforcing engagement of said bone screws with the spine.

11. An apparatus according to claim 1, further including means for attaching repositioning means to said first and second block portions.

12. An apparatus according to claim 11, wherein said repositioning means includes handles.

13. An apparatus for fixation to a human spine during spinal surgery, comprising:

a first block portion having opposite surfaces and opposite ends, one of said surfaces disposed to be fixed adjacent to a portion of the spine, a projecting portion extending from one said end, and at least two spaced apertures obliquely inclined relative to one another penetrating said first block portion between said opposite surfaces;

fixing means disposed in each of said apertures for fixing said first block portion to the spine, said fixing means including bone screws disposed in said spaced apertures, said screws being inclined relative to one another corresponding to the inclination of said apertures, wherein each said bone screw includes a head having an axial hole which in an upper portion of its extension is threaded, followed by a tapered portion and a key handle portion having an internal generally square configuration, an upper portion of the bone screw constituting a number of resilient segments, and a locking element having a key handle including an outer thread for cooperation with the threaded upper portion of the axial hole and a tapered portion for expanding the upper portion of the bone screw to be secured to the first block portion;

locking means for rigidly locking said fixing means within said apertures of said first block portion;

a second block portion disposed to be fixed to another portion of the spine; and attachment means for attaching said second block portion to said projecting portion in spaced relation to said first block portion, said attachment means including means for adjusting the space between said first and second block portions.

14. An apparatus according to claim 13, wherein the key handle and the locking element of each bone screw are of the same dimension.

15. An apparatus according to claim 13, wherein the first block portion includes two members pivotally connected to each other, one of said members having the bone screws and the other said member rotatably mounting a screw spindle, further including locking means for locking said members in relation to each other, having a second key handle operable from the same direction as the key handle of the bone screw.

16. An apparatus according to claim 15, wherein the members are pivotally connected to each other by means of a bolt having a head about which one said member is freely rotatable, penetrated by a transverse elongated hole in an axial direction, the axially extending edge portions thereof being bevelled, an end portion having a taper matching a tapered portion of the locking means, a threaded portion extending through the other member, said end portion of the hole being situated at a distance from the head such that the tapered portion of the locking means contacts the end portion and brings forth a relative displacement in an axial direction between the bolt and the member, pressing the members towards each other.

17. An apparatus according to claim 15, wherein surfaces of one member have radial grooves forming ridges which engage with corresponding ridges on said other member to lock the members in a desired angular position, said members forming an angle relative to each other.

* * * * *